US011399719B2

(12) United States Patent
Irisawa et al.

(10) Patent No.: US 11,399,719 B2
(45) Date of Patent: Aug. 2, 2022

(54) PROBE FOR PHOTOACOUSTIC MEASUREMENT AND PHOTOACOUSTIC MEASUREMENT APPARATUS INCLUDING SAME

(71) Applicant: FUJIFILM Corporation, Tokyo (JP)

(72) Inventors: Kaku Irisawa, Ashigarakami-gun (JP); Atsushi Hashimoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 348 days.

(21) Appl. No.: 15/220,619

(22) Filed: Jul. 27, 2016

(65) Prior Publication Data

US 2016/0331243 A1  Nov. 17, 2016

Related U.S. Application Data

(63) Continuation of application No. PCT/JP2014/080716, filed on Nov. 20, 2014.

(30) Foreign Application Priority Data

Jan. 28, 2014  (JP) .............................. JP2014-013063

(51) Int. Cl.
*A61B 5/00* (2006.01)
*A61B 8/08* (2006.01)
*A61B 8/00* (2006.01)

(52) U.S. Cl.
CPC .......... *A61B 5/0095* (2013.01); *A61B 8/0891* (2013.01); *A61B 8/4444* (2013.01);
(Continued)

(58) Field of Classification Search
CPC ... A61B 5/0095; A61B 8/0891; A61B 8/4444; A61B 8/4416; A61B 2562/0242; A61B 2562/146; A61B 8/5269
See application file for complete search history.

(56) References Cited

U.S. PATENT DOCUMENTS 6,069,698 A * 5/2000 Ozawa ................. A61B 5/0062
356/511
6,846,288 B2 * 1/2005 Nagar .................. A61B 5/0095
600/316
(Continued)

FOREIGN PATENT DOCUMENTS

CN      103501691 A    1/2014
JP      2012-166009 A  9/2012
(Continued)

OTHER PUBLICATIONS

Jaillon et al, Half-ball lens couples a beveled fiber probe for depth-resolved spectroscopy: Monte Carlo simulations, 2008, Applied Optics vol. 47, Issue 17, pp. 3152-3157 (Year: 2008).*
(Continued)

*Primary Examiner* — Ashley K Buran
*Assistant Examiner* — Amy J Shafqat
(74) *Attorney, Agent, or Firm* — Birch, Stewart, Kolasch & Birch, LLP (57) ABSTRACT

Disclosed are a probe for photoacoustic measurement which can suppress generation of artifacts obstructive to signal observation in a photoacoustic measurement, and a photoacoustic measurement apparatus including the same. The probe for photoacoustic measurement includes a light emission unit which emits measurement light to a subject, and an acoustic wave detection unit which detects a photoacoustic wave generated in the subject by the emission of measurement light. An emission end surface of the light emission unit is positioned to a side where the acoustic wave detection unit is located, with respect to a contact plane of the probe, and an optical axis at the emission end surface is inclined to a side opposite to the side on which the acoustic wave detection unit is positioned with respect to a normal direc-
(Continued)

tion of a detection surface of the acoustic wave detection unit.

11 Claims, 8 Drawing Sheets

(52) U.S. Cl.
CPC ..... *A61B 8/4416* (2013.01); *A61B 2562/0242* (2013.01); *A61B 2562/146* (2013.01)

(56) References Cited

U.S. PATENT DOCUMENTS

| | | | | |
|---|---|---|---|---|
| 6,872,433 | B2* | 3/2005 | Seward | A61L 29/126 428/35.7 |
| 7,620,445 | B2* | 11/2009 | Tsujita | A61B 5/0066 600/467 |
| 9,161,684 | B2* | 10/2015 | Seibel | A61B 1/0661 |
| 10,258,241 | B2* | 4/2019 | Zalev | A61B 5/14542 |
| 10,682,061 | B2* | 6/2020 | Reza | G01N 21/1717 |
| 2004/0215072 | A1* | 10/2004 | Zhu | A61B 5/0091 600/407 |
| 2005/0105096 | A1* | 5/2005 | Fee | A61B 5/0086 356/477 |
| 2006/0184042 | A1* | 8/2006 | Wang | A61B 5/0073 600/476 |
| 2007/0239006 | A1* | 10/2007 | Kamiyama | A61B 8/4254 600/437 |
| 2008/0177183 | A1* | 7/2008 | Courtney | A61B 5/0035 600/463 |
| 2011/0224532 | A1 | 9/2011 | Tanabe | |
| 2011/0303015 | A1* | 12/2011 | Ichihara | A61B 5/0091 73/656 |
| 2013/0109941 | A1* | 5/2013 | Li | G01N 21/49 600/407 |
| 2013/0112001 | A1* | 5/2013 | Furukawa | A61B 5/0095 73/655 |
| 2013/0160558 | A1* | 6/2013 | Oishi | A61B 5/0059 73/655 |
| 2013/0261426 | A1* | 10/2013 | Irisawa | A61B 5/0095 600/407 |
| 2013/0289381 | A1* | 10/2013 | Oraevsky | A61B 5/7425 600/407 |
| 2013/0310694 | A1 | 11/2013 | Tsujita et al. | |
| 2014/0046166 | A1* | 2/2014 | Tokita | A61B 5/0095 600/407 |
| 2014/0051971 | A1* | 2/2014 | Tokita | A61B 5/0095 600/407 |
| 2014/0114170 | A1* | 4/2014 | Tokita | A61B 5/0095 600/407 |
| 2014/0221810 | A1* | 8/2014 | Kacprowicz | A61B 5/0095 600/407 |
| 2015/0005613 | A1* | 1/2015 | Kim | A61B 5/0095 600/407 |
| 2015/0135839 | A1* | 5/2015 | Lee | G01N 21/1702 73/643 |
| 2015/0173626 | A1* | 6/2015 | Irisawa | G01N 29/2418 600/407 |
| 2017/0049331 | A1* | 2/2017 | Suzuki | A61B 5/0095 |
| 2017/0310889 | A1* | 10/2017 | Seibel | A61B 1/07 |
| 2018/0146859 | A1* | 5/2018 | Oyama | A61B 8/463 |
| 2018/0338686 | A1* | 11/2018 | Tokita | A61B 5/6844 |

FOREIGN PATENT DOCUMENTS

| | | |
|---|---|---|
| JP | 2012-179350 A | 9/2012 |
| JP | 2013-27482 A | 2/2013 |
| JP | 2013255707 A * | 12/2013 |
| WO | WO 2012/150656 A1 | 11/2012 |

OTHER PUBLICATIONS

WO2015114919 WIPO Full Text Machine Translation, accessed Oct. 22, 2021.*
Chinese Office Action, dated May 8, 2018, for corresponding Chinese Application No. 201480074258.4, with English translation.
Extended European Search Report, dated Jan. 18, 2017, for European Application No. 14881381.9.
International Search Report for PCT/JP2014/080716 (PCT/ISA/210) dated Feb. 17, 2015.
Written Opinion of the International Searching Authority for PCT/JP2014/080716 (PCT/ISA/237) dated Feb. 17, 2015.
English Translation of International Preliminary Report on Patentability (including PCT/IB/373 and PCT/ISA/237) for PCT/JP2014/080716, dated Aug. 2, 2016.
European Office Action dated Apr. 7, 2020, for corresponding European Application No. 14881381.9.

* cited by examiner

PROBE FOR PHOTOACOUSTIC MEASUREMENT AND PHOTOACOUSTIC MEASUREMENT APPARATUS INCLUDING SAME

CROSS-REFERENCE TO RELATED APPLICATIONS

This application is a Continuation of PCT International Application No. PCT/JP2014/080716 filed on Nov. 20, 2014, which claims priority under 35 U.S.C § 119(a) to Japanese Patent Application No. 2014-013063 filed on Jan. 28, 2014. Each of the above application(s) is hereby expressly incorporated by reference, in its entirety, into the present application.

BACKGROUND OF THE INVENTION

1. Field of the Invention

The present invention relates to a probe for photoacoustic measurement which performs a measurement based on a photoacoustic signal generated in a subject, and a photoacoustic measurement apparatus including the same.

2. Description of the Related Art

In recent years, a noninvasive measurement method using a photoacoustic effect has been attracting attention. This measurement method irradiates a subject with pulse light having a predetermined wavelength (for example, the wavelength range of visible light, near-infrared light, or middle infrared light), detects an ultrasonic wave (photoacoustic wave) which is an elastic wave generated when an absorbing material in the subject absorbs the energy of pulse light, and quantitatively measures the concentration of the absorbing material. Examples of the absorbing material in the subject include glucose or hemoglobin in the blood. Furthermore, a technique which detects the photoacoustic wave and generates a photoacoustic image based on the detection signal is referred to as photoacoustic imaging (PAI) or photoacoustic tomography (PAT).

In conventional photoacoustic imaging, a probe which guides light to the vicinity of both sides of a transducer array using a light guide member, such as a light guide plate, has been suggested (for example, JP2012-166009A and JP2012-179350A).

SUMMARY OF THE INVENTION

On the other hand, the inventors have found that, in a case where a probe provided with a light guide member and a transducer array in parallel with each other is used, a photoacoustic wave which is generated in a surface portion of a subject, on which measurement light is incident, propagates on the subject surface and is detected by the transducer array together with other signals, and causes an artifact (virtual image). The presence of an artifact may become an obstacle when observing a photoacoustic signal from a measurement target.

The invention has been accomplished in consideration of the above-described problem, and an object of the invention is to provide a probe for photoacoustic measurement which can suppress generation of artifacts obstructive to signal observation in a photoacoustic measurement, and a photoacoustic measurement apparatus including the same.

In order to solve the above-described problem, a probe for photoacoustic measurement of the invention comprises a light emission unit which emits measurement light to a subject, and an acoustic wave detection unit which detects a photoacoustic wave generated in the subject by the emission of the measurement light. An emission end surface of the light emission unit is positioned to a side where the acoustic wave detection unit is located, with respect to a contact plane of the probe, and an optical axis at the emission end surface is inclined to a side opposite to the side on which the acoustic wave detection unit is positioned with respect to a normal direction of a detection surface of the acoustic wave detection unit.

In the invention, the term "contact plane" means a plane which passes through the tip of the probe (that is, an intersection point of a probe surface in contact with the subject and a central axis of the acoustic wave detection unit) and is parallel to a detection surface of the acoustic wave detection unit.

In the probe for photoacoustic measurement of the invention, it is preferable that an optical axis at the emission end surface is inclined by reflection or refraction the measurement light.

In the probe for photoacoustic measurement of the invention, it is preferable that the acoustic wave detection unit is a transducer array having a plurality of acoustic wave detection elements, and the light emission unit includes a first light guide member which expands a propagation range of the measurement light in an array direction of the transducer array.

In a case where the light emission unit includes the first light guide member, it is preferable that an optical axis in the first light guide member is parallel to the normal direction.

The optical axis at the emission end surface may be inclined by refraction of the measurement light when emitted from the first light guide member.

Alternatively, in the probe for photoacoustic measurement of the invention, the light emission unit may have an optical member which inclines the optical axis at the emission end surface by reflecting or refracting the measurement light emitted from the first light guide member.

In a case where the optical axis is inclined by the first light guide member or the optical member, it is preferable that the light emission unit includes a second light guide member which has the emission end surface of the light emission unit, and the second light guide member has a diffusion unit which diffuses the measurement light.

Alternatively, in the probe for photoacoustic measurement of the invention, the light emission unit may include a second light guide member which has the emission end surface of the light emission unit, and the emission end surface of the second light guide member may incline the optical axis at the emission end surface by refracting the measurement light when emitted from the second light guide member. In this case, it is preferable that the second light guide member has a diffusion unit which diffuses the measurement light.

A photoacoustic measurement apparatus of the invention comprises a probe having a light emission unit configured to emit measurement light to a subject and an acoustic wave detection unit configured to detect a photoacoustic wave generated in the subject by the emission of the measurement light, and a signal processing unit which processes a photoacoustic signal based on the photoacoustic wave detected by the acoustic wave detection unit. An emission end surface of the light emission unit is positioned to a side where the acoustic wave detection unit is located, with respect to a contact plane of the probe, and an optical axis at the emission end surface is inclined to a side opposite to the side on which the acoustic wave detection unit is positioned with respect to a normal direction of a detection surface of the acoustic wave detection unit.

In the photoacoustic measurement apparatus of the invention, it is preferable that an optical axis at the emission end surface is inclined by reflection or refraction of the measurement light.

In the photoacoustic measurement apparatus of the invention, it is preferable that the acoustic wave detection unit is a transducer array having a plurality of acoustic wave detection elements, and the light emission unit includes a first light guide member which expands a propagation range of the measurement light in an array direction of the transducer array.

In a case where the light emission unit includes the first light guide member, it is preferable that an optical axis in the first light guide member is parallel to the normal direction.

The optical axis at the emission end surface may be inclined by refraction of the measurement light when emitted from the first light guide member.

Alternatively, in the photoacoustic measurement apparatus of the invention, the light emission unit may have an optical member which inclines the optical axis at the emission end surface by reflecting or refracting the measurement light emitted from the first light guide member.

In a case where the optical axis is inclined by the first light guide member or the optical member, it is preferable that the light emission unit includes a second light guide member which has the emission end surface of the light emission unit, and the second light guide member has a diffusion unit which diffuses the measurement light.

Alternatively, in the photoacoustic measurement apparatus of the invention, the light emission unit may include a second light guide member which has the emission end surface of the light emission unit, and the emission end surface of the second light guide member may incline the optical axis at the emission end surface by refracting the measurement light when emitted from the second light guide member. In this case, it is preferable that the second light guide member has a diffusion unit which diffuses the measurement light.

According to the probe for photoacoustic measurement of the invention and the photoacoustic measurement apparatus including the same, the emission end surface of the light emission unit is positioned to the side where the acoustic wave detection unit is located, with respect to the contact plane of the probe, and the optical axis at the emission end surface is inclined to the side opposite to the side on which the acoustic wave detection unit is positioned with respect to the normal direction of the detection surface of the acoustic wave detection unit; thus, it is possible to reduce the amount of measurement light emitted to the region of the subject in the vicinity of the acoustic wave detection unit. With this, it is possible to suppress generation of photoacoustic waves in the surface portion of the subject in the vicinity of the acoustic wave detection unit. As a result, it is possible to suppress generation of artifacts obstructive to signal observation in a photoacoustic measurement.

DESCRIPTION OF THE PREFERRED EMBODIMENTS

Hereinafter, an embodiment of the invention will be described referring to the drawings, but the invention is not limited to the embodiment. For ease of visual recognition, the scale and the like of each of components in the drawings are made to be appropriately different from the actual scale and the like.

First Embodiment

Figure 1:
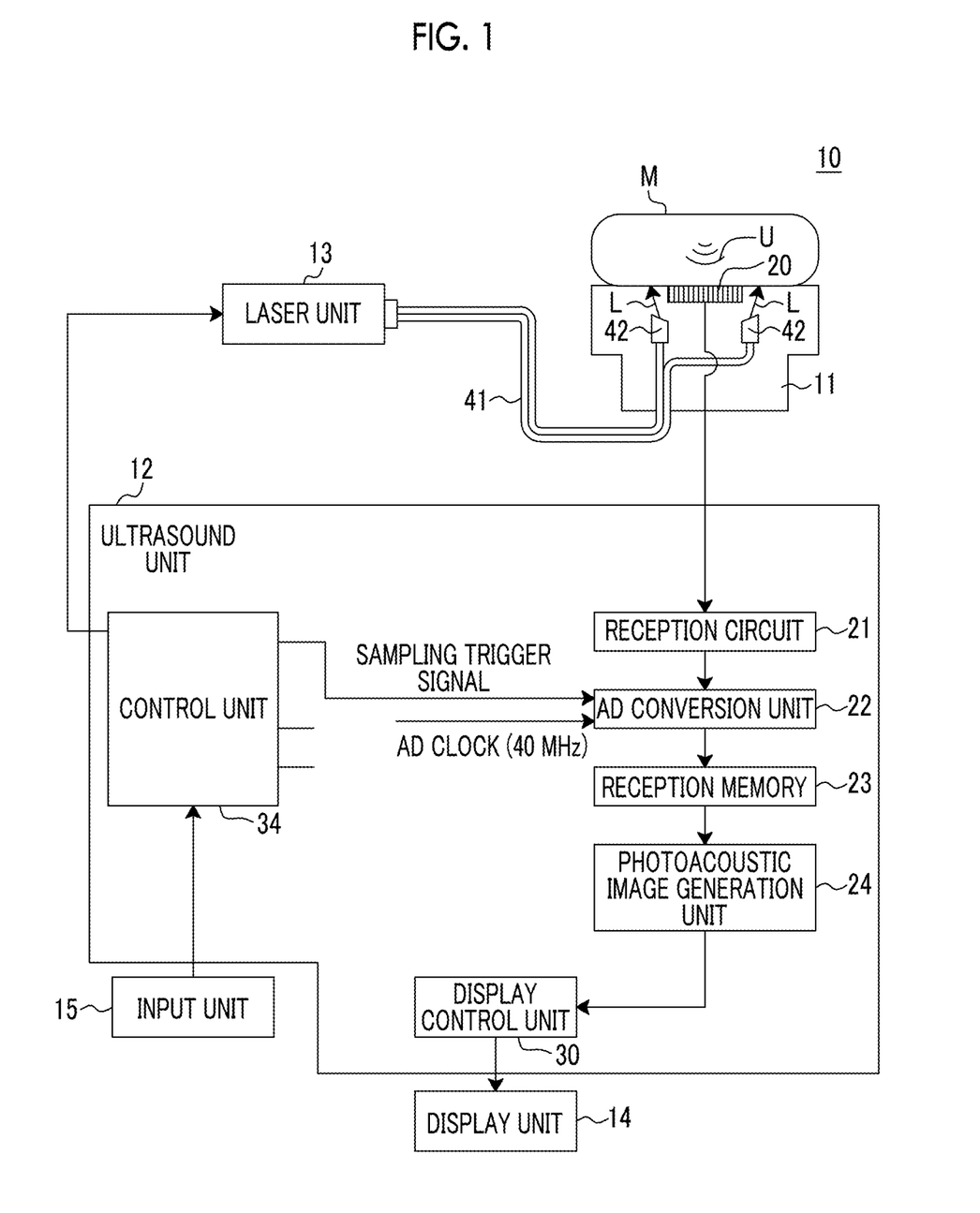
FIG. 1 is a schematic view showing the configuration of a photoacoustic measurement apparatus of a first embodiment.
Figure 2A:
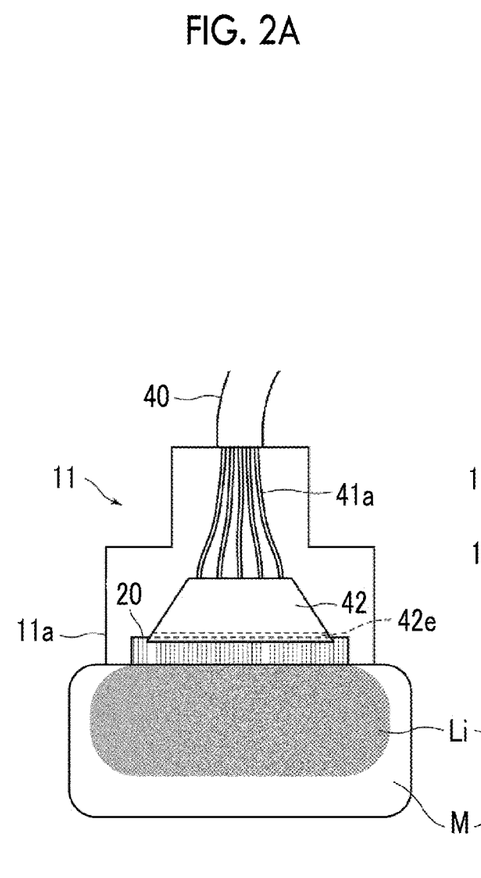
FIGS. 2A and 2B are schematic views showing the configuration of a probe of the first embodiment.
Figure 2B:
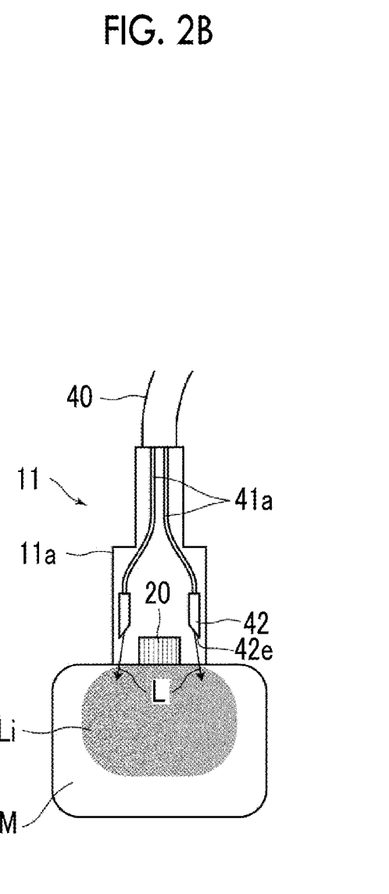

First, a probe for photoacoustic measurement of a first embodiment and a photoacoustic measurement apparatus including the same will be described. FIG. 1 is a schematic view showing the configuration of the photoacoustic measurement apparatus of this embodiment. FIGS. 2A and 2B are schematic views showing the configuration of a probe, and specifically, FIG. 2A is a sectional view of the probe when viewed from the front and FIG. 2B is a sectional view of the probe when viewed from the side.

A photoacoustic measurement apparatus 10 of this embodiment has a photoacoustic image generation function of, for example, generating a photoacoustic image based on a photoacoustic signal. Specifically, as shown in FIG. 1, the photoacoustic measurement apparatus 10 of this embodiment comprises a probe 11, an ultrasound unit 12, a laser unit 13, a display unit 14, and an input unit 15.

Probe

The probe 11 irradiates a subject with an ultrasonic wave or detects an acoustic wave U propagating through a subject M. That is, the probe 11 can perform irradiation (transmission) of an ultrasonic wave to the subject M and detection (reception) of a reflected ultrasonic wave (reflected acoustic wave) reflected from the subject M. The probe 11 can perform detection of a photoacoustic wave generated in the subject M when an absorbent in the subject M absorbs a laser beam. In this specification, the term "acoustic wave" has a meaning including an ultrasonic wave and a photoacoustic wave. The term "ultrasonic wave" means an elastic wave transmitted from the probe and a reflected wave of the elastic wave, and the term "photoacoustic wave" means an elastic wave generated in the subject M by a photoacoustic effect according to irradiation of measurement light. Examples of the absorbent include a blood vessel, a metal member, and the like.

For example, as shown in FIGS. 1, 2A, and 2B, the probe 11 of this embodiment comprises a transducer array 20, a bundle fiber 41 with a plurality of optical fiber wires 41a bundled, two light emission units 42 disposed with the transducer array 20 sandwiched therebetween, and a housing 11a including the transducer array 20, the bundle fiber 41, and the two light emission units 42.

The transducer array 20 has a plurality of ultrasound transducers (or acoustic wave detection elements) arranged in a one-dimensional or two-dimensional manner. In this embodiment, the transducer array 20 or each ultrasound transducer corresponds to an acoustic wave detection unit of the invention. Each ultrasound transducer is a piezoelectric element which is made of, for example, a polymer film, such as piezoelectric ceramics or polyvinylidene fluoride (PVDF). Each ultrasound transducer has a function of converting a reception signal to an electrical signal in a case where the acoustic wave U is received, and the electrical signal generated by the ultrasound transducer is output to a reception circuit 21 described below. The probe 11 is selected from a sector scanning type, a linear scanning type, and a convex scanning type according to an imaging region.

The bundle fiber 41 guides a laser beam from the laser unit 13 to the light emission units 42. The bundle fiber 41 is not particularly limited, and a known fiber, such as a quartz fiber, can be used. The bundle fiber 41 is branched into the optical fiber wires 41a on an emission side and is connected to the light emission units 42. For example, in a case where a light source is in the probe 11, and measurement light can be incident directly on the light emission units, or the like, the bundle fiber 41 is not required.

The light emission units 42 are sections which irradiate the subject M with laser beams guided by the bundle fiber 41. As shown in FIGS. 1 and 2B, in this embodiment, the two light emission units 42 are disposed on both sides of the transducer array 20 in an elevation direction (a direction perpendicular to the array direction of the transducer array and parallel to a detection surface) so as to face each other with the transducer array 20 sandwiched therebetween. Furthermore, in FIG. 2B, the light emission units 42 are disposed separately from a contact plane including the detection surface of the transducer array 20 upward (toward the transducer array side when viewed from the contact plane). With this, it is possible to secure the propagation distance of measurement light emitted from the light emission units. A part (for example, a corner of the emission end surface) of the emission end surface may be in contact with the contact plane.

Figure 3A:
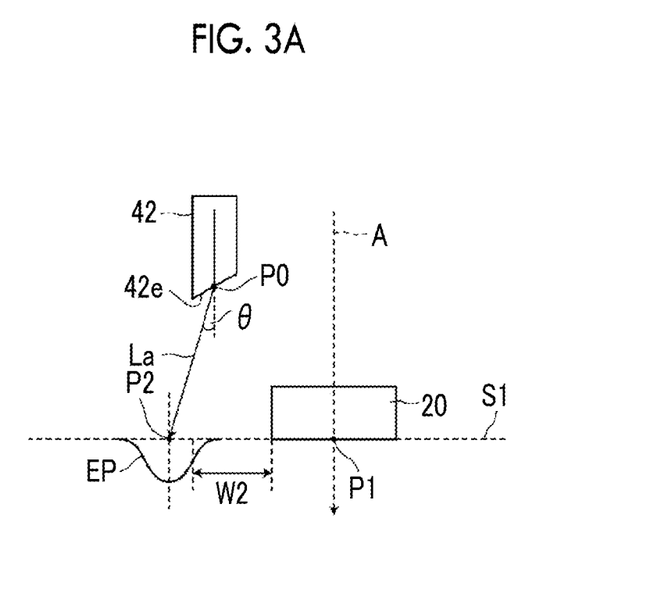
FIGS. 3A and 3B are schematic views showing the relationship between an optical axis in an emission end surface of a light emission unit and a contact plane of a probe.
Figure 3B:
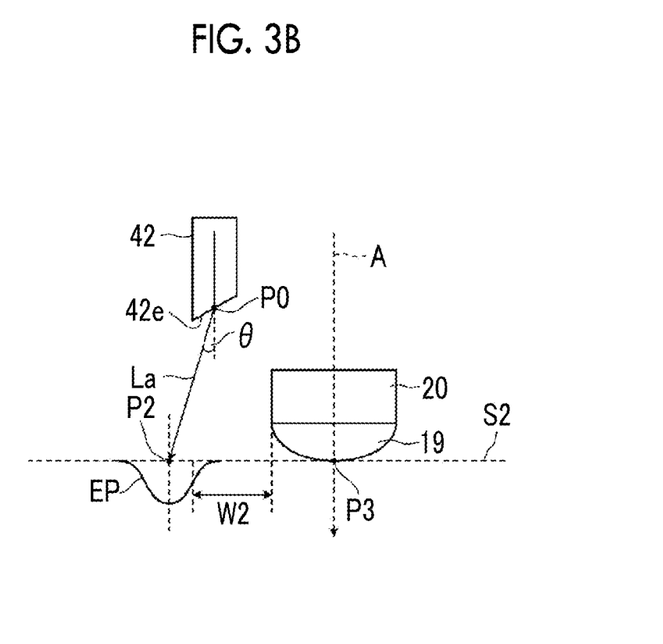

At an emission end of each of the light emission units 42, an emission end surface 42e which obliquely intersects an optical axis inside the light emission unit 42 is formed, and measurement light is refracted when emitted from the emission end surface 42e. "The emission end surface which obliquely intersects the optical axis" represents that the emission end surface 42e is not orthogonal to the optical axis and the emission end surface 42e and the optical axis intersect each other at an angle at which measurement light is refracted in a desired direction. With this, measurement light L is emitted from the light emission unit 42 in a state where the optical axis at the emission end surface is inclined to a side opposite to the side on which the transducer array 20 is positioned with respect to a normal direction of the detection surface of the transducer array 20 (acoustic wave detection unit). In other words, as shown in FIGS. 3A and 3B, an optical axis La at the emission end surface 42e is in a direction rotated by a predetermined angle θ to the side (hereinafter, referred to as an outer side of the probe) opposite to the side (hereinafter, referred to as an inner side of the probe) on which the transducer array 20 is positioned around an intersection point P0 of the emission end surface 42e and the optical axis inside the light emission unit 42 with respect to a normal direction A of the detection surface of the transducer array 20. That is, when the optical axis at the emission end surface is "inclined", this indicates that optical axis is direction in a direction rotated by the predetermined angle θ (0°<θ<90°) around the point P0 from the normal direction A in a side view of the probe 11. In FIGS. 3A and 3B, although the light emission unit 42 disposed on the right side of the transducer array 20 is not shown, in regard to the right light emission unit 42, the direction of the angle θ is reversed, that is, in regard to the right light emission unit 42, the optical axis is inclined in the right direction of FIGS. 3A and 3B.

In the invention, the term "optical axis" is specified in consideration of a line which will be the representative of an optical path from the standpoint of energy transmission of measurement light. For example, as shown in FIGS. 3A and 3B, a line which passes through the center of the light emission unit 42 can be specified as an optical axis in the light emission unit 42. Furthermore, for example, as shown in FIGS. 3A and 3B, a straight line which connects a central point P2 of a distribution when an energy profile EP of measurement light on a contact plane S1 is approximated by a Gaussian distribution and the point P0 can be specified as the optical axis La at the emission end surface 42e. As in FIG. 3A, in a case where nothing is mounted on the detection surface, a central point P1 of the transducer array 20 is defined as the tip of the probe, and a plane S1 which passes through the point P1 and is parallel to the detection surface is defined as a contact plane. On the other hand, for example, as in FIG. 3B, in a case where an acoustic member 19, such as an acoustic lens, is mounted on the detection surface, a tip portion P3 of the acoustic member 19 is defined as the tip of the probe, and a plane S2 which is in contact with the portion P3 and is parallel to the detection surface is defined as a contact plane. Furthermore, as in this embodiment, in a case where the acoustic wave detection unit has a plurality of acoustic wave detection elements, when the section of at least one acoustic wave detection element is viewed in a side view, the optical axis La at the emission end surface 42e has to be inclined to the outside with respect to the normal direction of the detection surface of the element. As in a convex probe, in a case where a transducer array has an arc shape, when the section perpendicular to the detection surface of each element is viewed, the optical axis La at the emission end surface 42e has to be inclined to the outside with respect to the normal direction of the detection surface of the element.

As the light emission units 42, for example, a light guide plate can be used. The light guide plate is, for example, a plate which is obtained by performing special processing on the surface of a plate made of resin or quartz and in which light incident on one end surface is uniformly emitted from the other end surface. As the resin, for example, acryl, polycarbonate, polystyrene, polyolefin, UV curable resin, or thermosetting resin can be used. In order to uniformly illuminate the subject surface on both sides of the transducer array 20, it is preferable that the light guide plate has a tapered shape with a thick tip and the width of the transducer array 20 in the array direction is nearly the same as the maximum width of the light guide plate. With this, it is possible to expand the propagation range of measurement light in the array direction of the transducer array 20. Furthermore, it is preferable that the maximum length of the light guide plate in the optical axis direction is 10 mm to 40 mm.

Laser Unit

The laser unit 13 has, for example, a Q switch solid-state laser source which emits a laser beam, and outputs a laser beam as measurement light L which is applied to the subject M. For example, the laser unit 13 is configured to receive a trigger signal from a control unit 34 of the ultrasound unit 12 and to output a laser beam. It is preferable that the laser unit 13 outputs pulse light having a pulse width of 1 nsec to 100 nsec as a laser beam. For example, in this embodiment, a light source of the laser unit 13 is a Q switch alexandrite laser.

The wavelength of the laser beam is appropriately determined by the optical absorption characteristics of an absorbent in a subject to be a measurement target. For example, in a case where the measurement target is hemoglobin in a living body (that is, in a case of imaging a blood vessel), in general, it is preferable that the wavelength is a wavelength which belongs to a near-infrared wavelength range. The near-infrared wavelength range means a wavelength range of about 700 to 850 nm. However, the wavelength of the laser beam is not, of course, limited thereto. The laser beam may be a single wavelength, or may include a plurality of wavelengths (for example, 750 nm and 800 nm). In a case where the laser beam includes a plurality of wavelengths, the subject M may be simultaneously irradiated with the beams having these wavelengths or may be irradiated with the beams while the beams are alternately switched. The laser unit 13 may be a YAG-SHG-OPO laser or a Ti-Sapphire laser, which can output a laser beam in a near-infrared wavelength range, other than the alexandrite laser.

Ultrasound Unit

The ultrasound unit 12 has a reception circuit 21, an AD conversion unit 22, a reception memory 23, a photoacoustic image generation unit 24, a display control unit 30, and a control unit 34. The ultrasound unit 12 corresponds to a signal processing unit in the invention.

The control unit 34 controls the respective units of the photoacoustic measurement apparatus 10, and in this embodiment, comprises a trigger control circuit (not shown). The trigger control circuit sends a light trigger signal to the laser unit 13, for example, when activating the photoacoustic measurement apparatus. With this, in the laser unit 13, a flash lamp is turned on, and excitation of a laser rod is started. Then, the excitation state of the laser rod is maintained, and the laser unit 13 is placed in a state capable of outputting a pulse laser beam.

Thereafter, the control unit 34 transmits a Qsw trigger signal from the trigger control circuit to the laser unit 13. That is, the control unit 34 controls the output timing of the pulse laser beam from the laser unit 13 by the Qsw trigger signal. In this embodiment, the control unit 34 transmits a sampling trigger signal to the AD conversion unit 22 simultaneously with the transmission of the Qsw trigger signal. The sampling trigger signal becomes a sign of the start timing of sampling of a photoacoustic signal in the AD conversion unit 22. In this way, the sampling trigger signal is used, whereby it is possible to sample the photoacoustic signal in synchronization with the output of the laser beam.

The reception circuit 21 receives the photoacoustic signal detected by the probe 11. The photoacoustic signal received by the reception circuit 21 is transmitted to the AD conversion unit 22.

The AD conversion unit 22 samples the photoacoustic signal received by the reception circuit 21 to convert the photoacoustic signal to a digital signal. For example, the AD conversion unit 22 samples the photoacoustic signal in a predetermined sampling period based on an AD clock signal having a predetermined frequency input from the outside.

The reception memory 23 stores the photoacoustic signal sampled by the AD conversion unit 22. The reception memory 23 outputs data of the photoacoustic signal detected by the probe 11 to the photoacoustic image generation unit 24.

For example, the photoacoustic image generation unit 24 adds photoacoustic data stored in the reception memory 23 with a delay time according to the position of each ultrasound transducer to reconstruct data for one line, and generates data of a tomographic image (photoacoustic image) based on photoacoustic data of the respective lines. The photoacoustic image generation unit 24 may perform reconstruction using a circular back projection (CBP) method, instead of a delay addition method. The photoacoustic image generation unit 24 outputs data of the photoacoustic image generated as above to the display control unit 30.

The display control unit 30 displays the photoacoustic image on the display unit 14, such as a display, based on photoacoustic image data subjected to predetermined display processing by a display processing unit 25. In a case where the probe 11 has the transducer array arranged in a two-dimensional manner and a plurality of photoacoustic images are acquired by probe scanning, for example, the display control unit 30 may create volume data based on these photoacoustic images and may display a composite image on the display unit 14 as a three-dimensional image.

The input unit 15 is a section which is used when the user inputs photoacoustic measurement conditions and the like.

Figure 4:
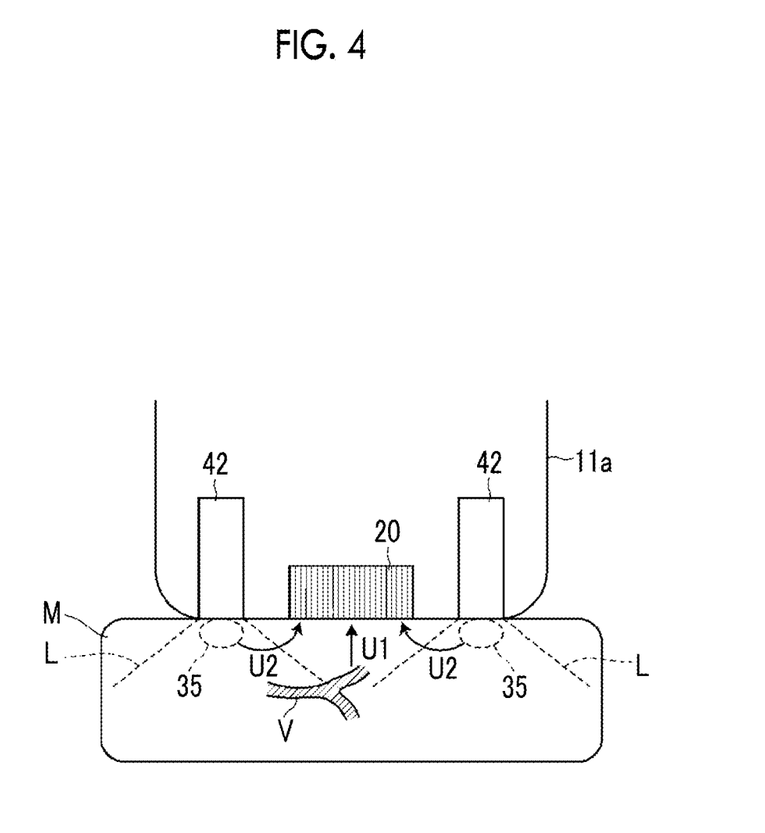
FIG. 4 is a schematic view showing a manner in which a photoacoustic wave generated from a blood vessel and a photoacoustic wave generated in a subject surface, on which measurement light is incident, are detected.

Hereinafter, the effects of the probe 11 and the photoacoustic measurement apparatus 10 of this embodiment will be described. The inventors have found that, in a case where a probe provided with a light emission unit and an acoustic wave detection unit in parallel with each other is used, a photoacoustic wave generated in the surface portion of the subject, on which measurement light is incident, propagates on the subject surface and is detected by the acoustic wave detection unit together with other signals, and causes an artifact (virtual image). For example, FIG. 4 is a schematic view showing a manner in which a photoacoustic wave generated from a blood vessel V and a photoacoustic wave generated in the subject surface, on which measurement light is incident, are detected. When measurement light L is applied to the subject M, ideally, only a photoacoustic wave U1 from the blood vessel V is detected; however, actually, a photoacoustic wave U2 generated in the subject surface portion 35, on which measurement light L is incident, is also detected. The photoacoustic wave U2 causes an artifact. The time from when the photoacoustic wave U2 is generated until the photoacoustic wave U2 is detected depends on the interval between an illumination region on a contact plane of measurement light L and the acoustic wave detection unit. That is, the larger the interval, the longer the distance at which the photoacoustic wave U2 propagates through the subject; thus, the time from when the photoacoustic wave U2 is generated until the photoacoustic wave U2 is detected is extended.

Figure 5A:
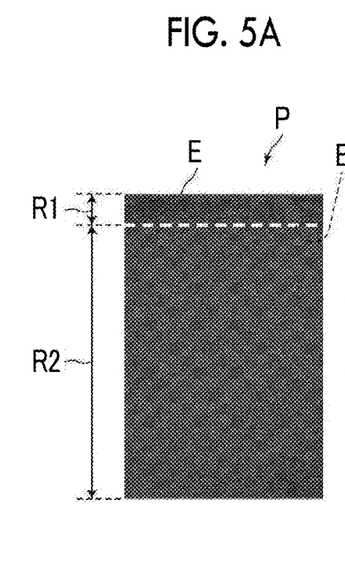
FIGS. 5A to 5D are diagrams showing a photoacoustic image in which an artifact region is caused by a photoacoustic wave generated in a subject surface.
Figure 5B:
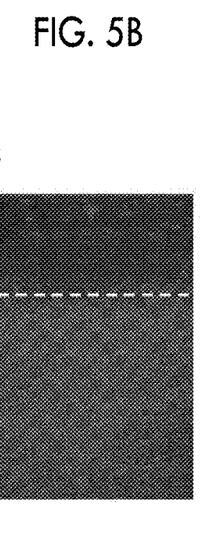
Figure 5C:
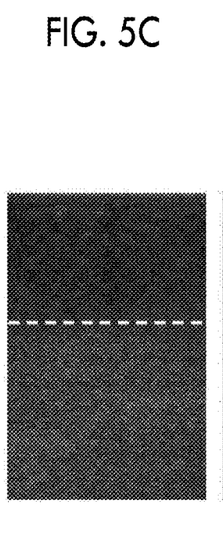
Figure 5D:
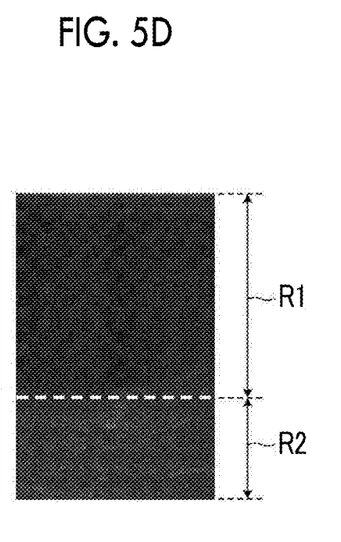
Figure 5E:
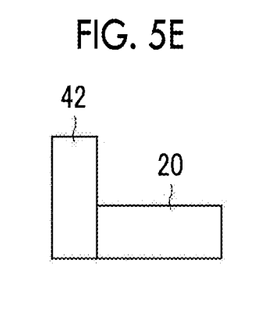
FIGS. 5E and 5F are schematic views showing the positional relationship between a light emission unit and a transducer array when the photoacoustic images of FIGS. 5A and 5D are generated.
Figure 5F:
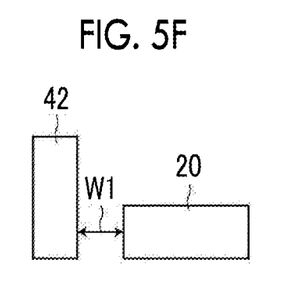

The time from when the photoacoustic wave U2 is generated until the photoacoustic wave U2 is detected affects a range in which an artifact appears in the photoacoustic image. FIGS. 5A to 5F are diagrams showing a change in size of an observation region R1 (a region where a signal from a measurement target, such as a blood vessel, can be identified and which primarily becomes an observation target) and an artifact region R2 depending on the interval W1 between the light emission unit 42 (light guide plate) and the transducer array 20. Specifically, FIGS. 5A to 5D are diagrams showing a photoacoustic image P in which the artifact region R2 is caused by the photoacoustic wave U2 generated in the subject surface. FIGS. 5E and 5F are respectively schematic views showing the positional relationship between the light emission unit 42 and the transducer array 20 when the photoacoustic images P of FIGS. 5A and 5D are generated. From FIGS. 5A to 5F, it is understood that the larger the interval W1 between the light emission unit 42 and the transducer array 20 (that is, the interval between the illumination region on the contact plane of measurement light L and the acoustic wave detection unit), the lower the boundary B between the observation region R1 and the artifact region R2. This is because the up-down direction of the photoacoustic image P corresponds to a time axis, and the larger the interval W1 between the light emission unit 42 and the transducer array 20, the later the time at which the signal of the photoacoustic wave U2 enters.

Accordingly, in the invention, the optical axis La at the emission end surface 42e is inclined to the outside of the probe, thereby reducing the amount of measurement light emitted to a region W2 (see FIGS. 3A and 3B) of the subject in the vicinity of the acoustic wave detection unit. With this, the amount of photoacoustic waves generated in the region W2 decreases, and the ratio of the observation region R1 to the artifact region R2 in the photoacoustic images shown in FIGS. 5A to 5D can be increased. The interval between the illumination region on the contact plane of measurement light L and the acoustic wave detection unit is appropriately set according to the depth of the observation region R1 desired to be secured. However, if the interval is too large, generation of an artifact in a deep region can be suppressed, while a sufficient amount of light does not reach a region directly below the acoustic wave detection unit, and the signal intensity of a photoacoustic wave desired to be originally detected is lowered. Accordingly, the interval is preferably about 3 mm to 20 mm, and particularly preferably, 10 mm to 15 mm. It is preferable that the inclination of the optical axis at the emission end surface 42e of the light emission unit 42 is set in a range in which the interval satisfies the range described above.

As above, in the probe for photoacoustic measurement of this embodiment and the photoacoustic measurement apparatus including the same, the emission end surface of the light emission unit is positioned to the side where the acoustic wave detection unit is located, with respect to the contact plane of the probe, and the optical axis at the emission end surface is inclined to the side opposite to the side on which the acoustic wave detection unit is positioned with respect to the normal direction of the detection surface of the acoustic wave detection unit; therefore, it is possible to reduce the amount of measurement light emitted to the region of the subject in the vicinity of the acoustic wave detection unit. As a result, it is possible to suppress generation of artifacts obstructive to signal observation in a photoacoustic measurement.

Design Change

In the first embodiment described above, although a case where each of the light emission units 42 has one light guide member has been described, the invention is not limited thereto. For example, FIGS. 6 to 9B are schematic views showing another configuration example of the light emission units 42.

Figure 6:
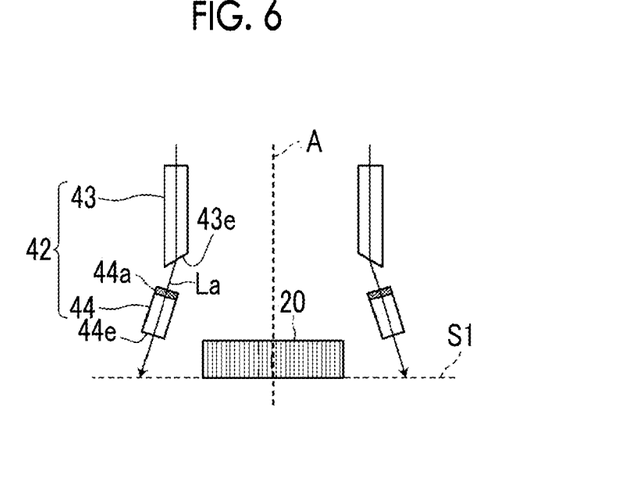
FIG. 6 is a schematic view showing another configuration example of a light emission unit.

Each of the light emission units 42 of FIG. 6 has a first light guide member 43 and a second light guide member 44, and measurement light guided by the optical fiber is guided so as to be transmitted through the first light guide member 43 and the second light guide member 44 in this order. The first light guide member 43 is provided in a state where an optical axis La inside the first light guide member 43 is parallel to a normal direction A of a detection surface, and the second light guide member 44 is provided in a state where an emission end surface 44e is separated from a contact plane S1. The term "parallel" has a meaning including an arrangement in which the first light guide member 43 is not completely parallel to the normal direction A of the detection surface and is inclined in a range of ±10° with respect to the normal direction A of the detection surface. An emission end surface 43e which obliquely intersects the optical axis inside the first light guide member 43 is formed at the emission end of the first light guide member 43, and measurement light is refracted when emitted from the emission end surface 43e. With this, the optical axis La at the emission end surface 43e is configured so as to be inclined to the outside of the probe 11. The second light guide member 44 receives measurement light emitted from the first light guide member 43 and causes measurement light to be emitted from the emission end surface 44e to the subject while maintaining the direction of the optical axis of measurement light at the time of incidence. That is, in a case of this configuration example, the emission end surface 44e of the second light guide member 44 corresponds to the emission end surface of the light emission unit 42 in the invention, and a predetermined inclination of the optical axis La at the emission end surface 44e is implement by refraction at the emission end surface 43e of the first light guide member 43. The maximum length of the first light guide member is preferably 10 mm to 40 mm, and the maximum length of the second light guide member is preferably 2 mm to 5 mm. The first light guide member 43 becomes long, whereby it is possible to further promote the spread of measurement light in the array direction before diffusing measurement light. Furthermore, a diffusion unit 44a which diffuses measurement light is provided at the incidence end of the second light guide member 44, whereby uniformity of illumination of measurement light is further improved. The diffusion unit 44a can be formed, for example, by providing a diffusion plate provided with multiple microlenses on the surface thereof, or by forming a layer including multiple scattering microparticles. The position where the diffusion unit 44a is provided is not particularly limited, and the diffusion unit 44a may be formed in an intermediate portion of the second light guide member or at the emission end of the second light guide member. From a standpoint of securing the propagation distance of diffused measurement light to improve uniformity of illumination, it is preferable that the diffusion unit 44a may be formed at the incidence end of the second light guide member.

Figure 7A:
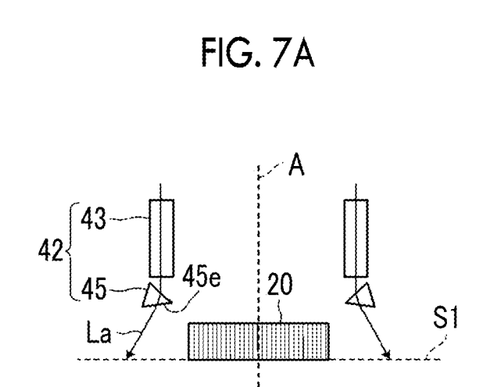
FIGS. 7A to 7C are schematic views showing another configuration example of a light emission unit.
Figure 7B:
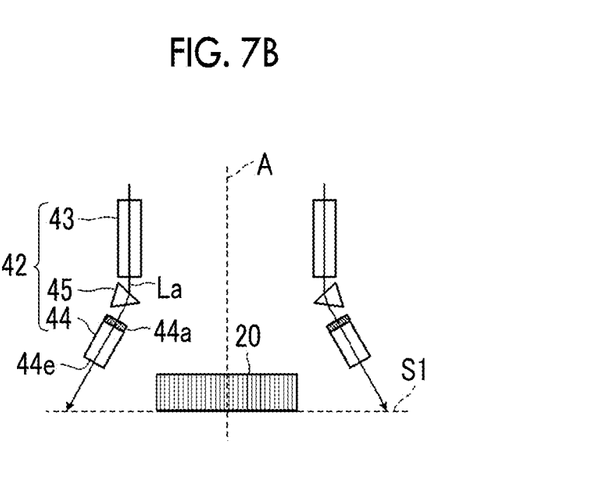
Figure 7C:
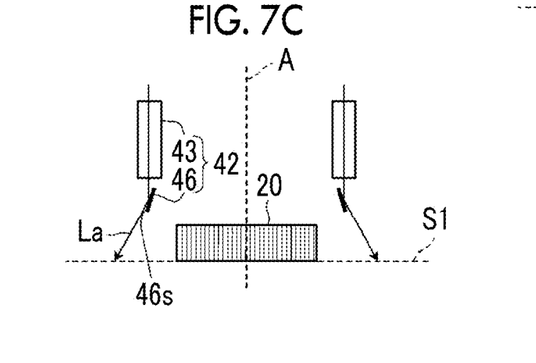

Each of the light emission units 42 of FIG. 7A has a first light guide member 43 and a prism member 45, and measurement light guided by the optical fiber is guided so as to be transmitted through the first light guide member 43 and the prism member 45 in this order. The prism member 45 is disposed in a state where an emission end surface 45*e* thereof is separated from the contact plane S1, and the arrangement or the length of the first light guide member 43 is the same as in FIG. 6. As shown in FIGS. 7A to 7C, an emission end surface 43*e* which obliquely intersects an optical axis La inside the first light guide member 43 is not formed at the emission end of the first light guide member 43, and measurement light is not refracted when emitted from the emission end surface 43*e*. Measurement light emitted from the first light guide member 43 is refracted when passing through the prism member 45, and an optical axis La at the emission end surface 45*e* of the prism member 45 is configured so as to be inclined to the outside of the probe 11. That is, in a case of this configuration example, the emission end surface 45*e* of the prism member 45 corresponds to the emission end surface of the light emission unit 42 in the invention, and a predetermined inclination of the optical axis La at the emission end surface 45*e* is implemented by refraction in the prism member 45. Each of the light emission units 42 of FIG. 7B is further provided with a second light guide member 44 at the back of the prism member, in addition to the configuration of FIG. 7A. The second light guide member 44 is the same as in FIG. 6. Each of the light emission units 42 of FIG. 7C is provided with a reflection member 46 (for example, a reflective film or a mirror), instead of the prism member 45 in the configuration of FIG. 7A. Measurement light guided by the optical fiber is transmitted through the first light guide member 43, and is then reflected from the reflection member 46. Measurement light emitted from the first light guide member 43 is reflected from the reflection member 46, and an optical axis La in a reflective surface 46*s* of the reflection member 46 is configured so as to be inclined to the outside of the probe 11. That is, in a case of this configuration example, an emission end surface 46*s* of the reflection member 46 corresponds to the emission end surface of the light emission unit 42 in the invention, and a predetermined inclination of the optical axis La at the emission end surface 46*s* is implemented by reflection in the reflection member 46. A second light guide member 44 may be provided in the configuration of FIG. 7C.

Figure 8A:
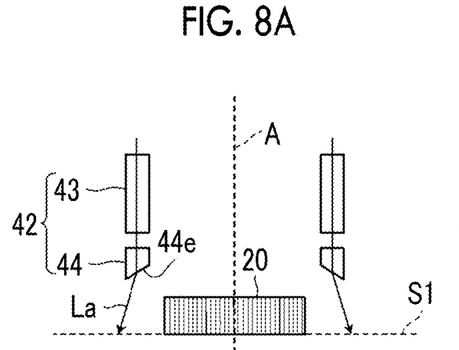
FIGS. 8A and 8B are schematic views showing another configuration example of a light emission unit.
Figure 8B:
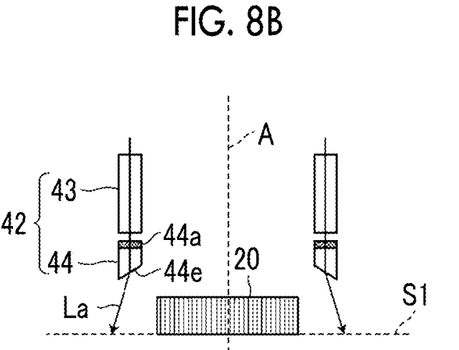
Figure 9A:
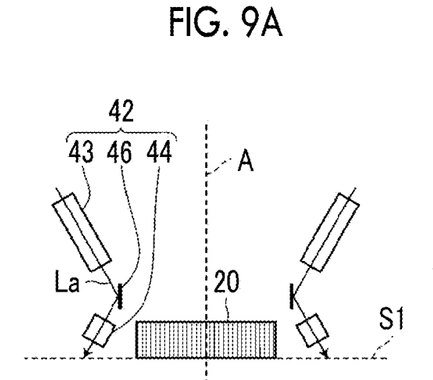
FIGS. 9A and 9B are schematic views showing another configuration example of a light emission unit.
Figure 9B:
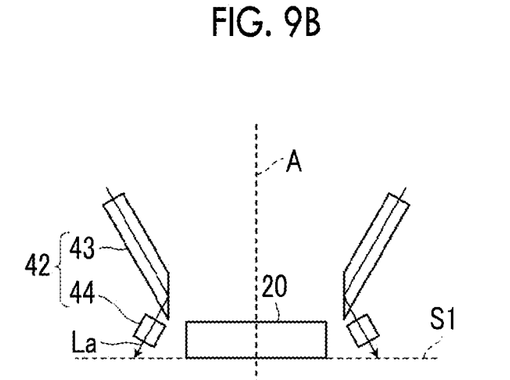

Each of the light emission units 42 of FIG. 8A also has a first light guide member 43 and a second light guide member 44, and measurement light guided by the optical fiber is guided so as to be transmitted through the first light guide member 43 and the second light guide member 44 disposed on the same straight line in this order. The configuration of each of the light emission units 42 of FIGS. 8A and 8B is different from the configuration of FIG. 6 in that an emission end surface 44*e* of the second light guide member 44, instead of the first light guide member 43, is processed obliquely with respect to the optical axis. Accordingly, measurement light is refracted from the emission end surface 44*e* when emitted from the second light guide member, and an optical axis La at the emission end surface 44*e* is configured so as to be inclined to the outside of the probe 11. That is, in a case of this configuration example, the emission end surface 44*e* of the second light guide member 44 corresponds to the emission end surface of the light emission unit 42 in the invention, and a predetermined inclination of the optical axis La at the emission end surface 44*e* is implemented by refraction at the emission end surface 44*e*. Each of the light emission units 42 of FIG. 8B is further provided with a diffusion unit 44*a* in the second light guide member 44 in the configuration of FIG. 8A. The diffusion unit 44*a* is the same as in FIG. 6.

In the configuration examples of FIGS. 6 to 8B, since the first light guide member 43 is provided in a state where the optical axis La inside the first light guide member 43 is parallel to the normal direction A of the detection surface, there is an advantage that the probe is reduced in size and uniformity of illumination is satisfactory since the first light guide member 43 is used. In particular, as shown in FIG. 6 or 8A and 8B, in a case where an inclined surface (for example, the emission end surface 43*e* or 44*e*) with respect to the optical axis is formed in at least one of the first light guide member 43 and the second light guide member 44, an optical member (for example, the prism member of FIG. 7B) which inclines the optical axis is not required; thus, there is an advantage that the arrangement adjustment of the members is facilitated. The inclined surface with respect to the optical axis may be formed at the emission ends of both of the first light guide member 43 and the second light guide member 44. In this case, a target inclination of the optical axis at the emission end surface of the light emission unit is implemented by gradual refraction of measurement light from the respective emission end surfaces.

In the configuration examples of FIGS. 6 to 8B, although a case where the optical axis La inside the first light guide member 43 is parallel to the normal direction A has been described, the invention is not limited thereto. For example, each of the light emission units 42 of FIG. 9A has a first light guide member 43 in which an optical axis La is inclined to the inner side of the probe, a reflection member 46, and a second light guide member 44. Measurement light is reflected from the reflection member 46, whereby an optical axis La in a reflective surface is configured so as to be inclined to the outer side of the probe 11. In this configuration example, there is an advantage that inexpensive members can be used and uniformity of illumination is satisfactory since the first light guide member 43 is disposed obliquely and a comparatively long first light guide member can be used. Each of the light emission units 42 of FIG. 9B has a first light guide member 43 and a second light guide member 44, the first light guide member 43 is processed obliquely to form a surface, and measurement light propagating therethrough is reflected from this surface. In this configuration example, there is an advantage that the arrangement adjustment of the members is facilitated since the number of components is decreased compared to the light emission units 42 of FIG. 9A and uniformity of illumination is satisfactory since the first light guide member 43 is obliquely disposed and a comparatively long first light guide member can be used compared to the light emission units 42 of FIGS. 6 to 8B.

Figure 10:
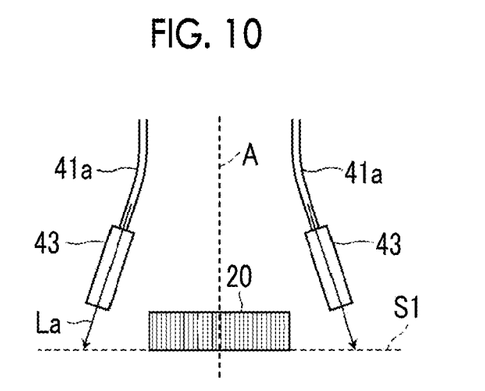
FIG. 10 is a schematic view showing another method of inclining an optical axis.

The invention is not limited to a case where an optical axis of a predetermined inclination is implemented by the light emission units 42. For example, as shown in FIG. 10, the arrangement of optical fibers 41*a* may be adjusted to adjust the optical axis of measurement light to have a predetermined inclination before entering the light emission units 42.

Second Embodiment

Figure 11:
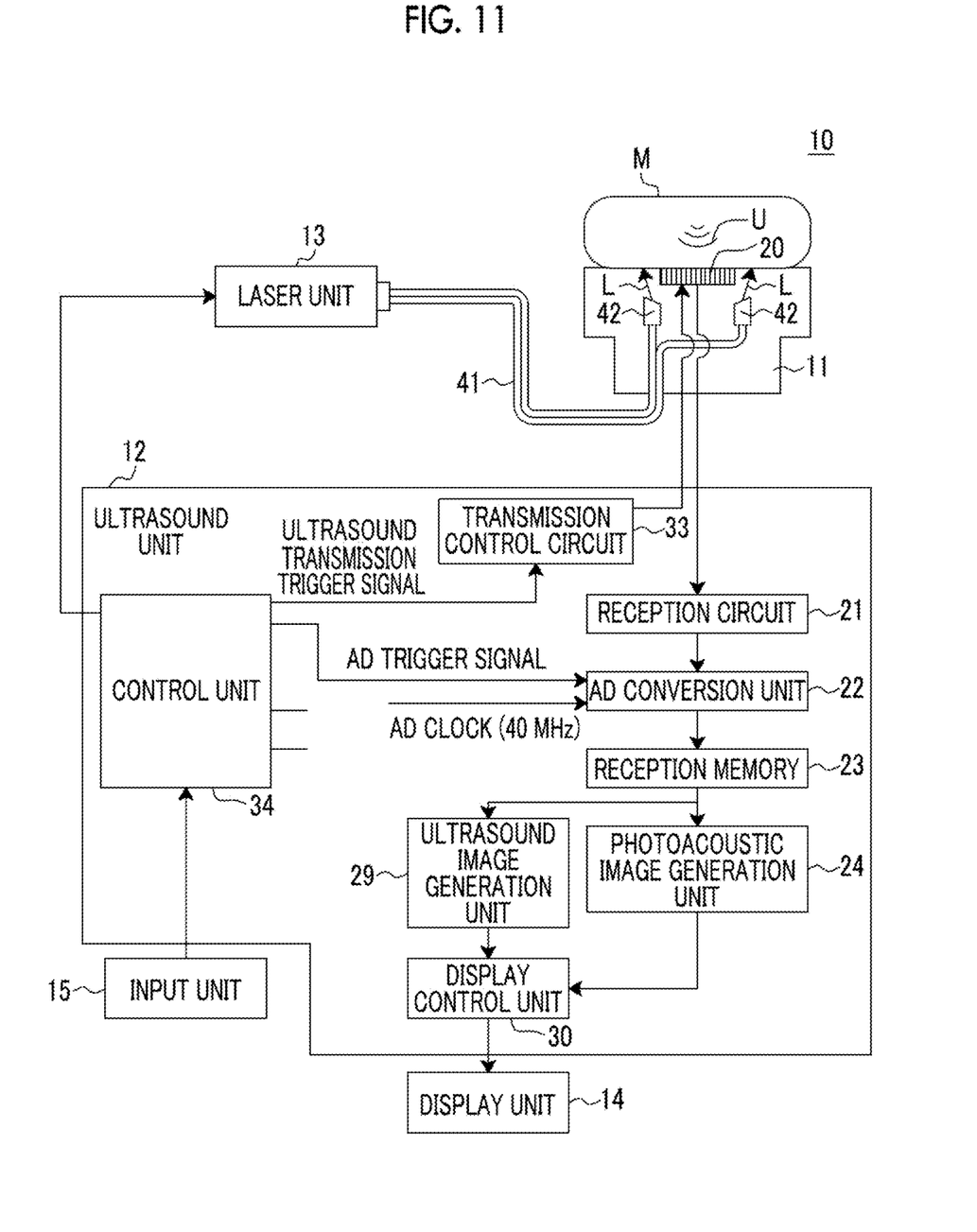
FIG. 11 is a schematic view showing the configuration of a photoacoustic measurement apparatus of a second embodiment.

Next, a probe for photoacoustic measurement of a second embodiment and a photoacoustic measurement apparatus including the same will be described. FIG. 11 is a schematic view showing the configuration of the photoacoustic measurement apparatus of this embodiment. This embodiment is different from the first embodiment in that an ultrasound image is generated in addition to a photoacoustic image. Therefore, detailed description of the same components as those in the first embodiment will not be repeated unless particularly necessary.

As shown in FIG. 11, a photoacoustic measurement apparatus 10 of this embodiment comprises a probe 11, an ultrasound unit 12, a laser unit 13, a display unit 14, and an input unit 15.

Ultrasound Unit

The ultrasound unit 12 of this embodiment comprises an ultrasound image generation unit 29 and a transmission control circuit 33, in addition to the configuration of the photoacoustic measurement apparatus shown in FIG. 1.

In this embodiment, the probe 11 performs the output (transmission) of an ultrasonic wave to the subject and the detection (reception) of a reflected ultrasonic wave (reflected acoustic wave) of the transmitted ultrasonic wave from the subject, in addition to the detection of the photoacoustic signal. As an ultrasound transducer which performs transmission and reception of an ultrasonic wave, the transducer array 20 in the invention may be used, or a new ultrasound transducer which is provided in a different probe 11 for transmission and reception of an ultrasonic wave may be used. Transmission and reception of an ultrasonic wave may be performed separately. For example, transmission of an ultrasonic wave may be performed from a position different from the probe 11, and a reflected ultrasonic wave of the transmitted ultrasonic wave may be received by the probe 11.

The control unit 34 sends an ultrasonic transmission trigger signal to the effect of instructing the transmission control circuit 33 to perform ultrasonic transmission at the time of the generation of an ultrasound image. If the trigger signal is received, the transmission control circuit 33 transmits an ultrasonic wave from the probe 11. The probe 11 detects a reflected ultrasonic wave from the subject after transmitting the ultrasonic wave.

The reflected ultrasonic wave detected by the probe 11 is input to the AD conversion unit 22 through the reception circuit 21. The control unit 34 sends a sampling trigger signal to the AD conversion unit 22 according to the timing of ultrasonic transmission to start sampling of the reflected ultrasonic wave. The AD conversion unit 22 stores the sampling signal of the reflected ultrasonic wave in the reception memory 23. Either sampling of the photoacoustic signal or sampling of the reflected ultrasonic wave may be performed earlier.

The ultrasound image generation unit 29 performs signal processing, such as reconstruction processing, detection processing, and logarithmic conversion processing, based on (the sampling signal of) the reflected ultrasonic wave detected by the transducer array 20 of the probe 11 to generate data of an ultrasound image. For the generation of image data, similarly to the generation of image data in the photoacoustic image generation unit 24, a delay addition method or the like can be used.

For example, the display control unit 30 displays the photoacoustic image and the ultrasound image individually or a composite image of the photoacoustic image and the ultrasound image on the display unit 14. For example, the display control unit 30 performs image composition by superimposing the photoacoustic image and the ultrasound image on each other.

In this embodiment, the photoacoustic measurement apparatus generates the ultrasound image in addition to the photoacoustic image. Therefore, in addition to the effects of the second embodiment, it is possible to observe a portion, which cannot be imaged in the photoacoustic image, with reference to the ultrasound image.

EXPLANATION OF REFERENCES

10: photoacoustic measurement apparatus
11: probe
12: ultrasound unit
13: laser unit
14: display unit
15: input unit
19: acoustic member
20: transducer array
21: reception circuit
22: conversion unit
23: reception memory
24: photoacoustic image generation unit
29: ultrasound image generation unit
30: display control unit
33: transmission control circuit
34: control unit
41: bundle fiber
42: light emission unit
43: first light guide member
44: second light guide member
45: prism member
46: reflection member
L: measurement light
M: subject
U: acoustic wave

What is claimed is:

1. A photoacoustic measurement apparatus comprising:
a probe having a light emission unit configured to emit measurement light to a subject and an acoustic wave detection unit having a transducer array configured to detect a photoacoustic wave generated in the subject by the emission of the measurement light; and
a processor,
wherein the processor is configured to process a photoacoustic signal based on the photoacoustic wave detected by the acoustic wave detection unit,
wherein the probe includes a contact plane, the contact plane including a detection surface of the acoustic wave detection unit,
wherein an emission end surface of the light emission unit is spaced away from the contact plane of the acoustic wave detection unit toward an interior of the probe and toward the transducer array side in a normal direction of the detection surface, and
wherein the emission end surface is configured to direct light emitted from the light emission unit along an optical axis that is inclined away from a normal direction of the detection surface at a center of the acoustic wave detection unit, and
wherein the light emission unit reflects or refracts the measurement light to incline the optical axis at the emission end surface.

2. The photoacoustic measurement apparatus according to claim 1, wherein the acoustic wave detection unit is a transducer array having a plurality of acoustic wave detection elements, and
the light emission unit includes a first light guide member which expands a propagation range of the measurement light in an array direction of the transducer array.

3. The photoacoustic measurement apparatus according to claim 2, wherein an optical axis in the first light guide member is parallel to the normal direction.

4. The photoacoustic measurement apparatus according to claim 2, wherein the emission end surface of the light emission unit obliquely intersects an optical axis inside the light emission unit, and refracts the measurement light when emitted from the first light guide member to incline the optical axis at the emission end surface with respect to the normal direction.

5. The photoacoustic measurement apparatus according to claim 4, wherein the light emission unit includes a second light guide member which has the emission end surface of the light emission unit, and
the second light guide member has a diffusion unit which diffuses the r Measurement light.

6. The photoacoustic measurement apparatus according to claim 2, wherein the light emission unit includes a second light guide member which has the emission end surface of the light emission unit, and
the emission end surface of the second light guide member obliquely intersects an optical axis inside the second light guide member, and refracts the measurement light when emitted from the second light guide member to incline the optical axis at the emission end surface.

7. The photoacoustic measurement apparatus according to claim 6, wherein the second light guide member has a diffusion unit which diffuses the measurement light.

8. A photoacoustic measurement apparatus comprising:
a probe having a light emission unit configured to emit measurement light to a subject and an acoustic wave detection unit configured to detect a photoacoustic wave generated in the subject by the emission of the measurement light; and
a processor configured to process a photoacoustic signal based on the photoacoustic wave detected by the acoustic wave detection unit;
wherein
an emission end surface of the light emission unit is spaced away toward an interior of the probe from a contact plane of the acoustic wave detection unit in a normal direction of a detection surface of the acoustic wave detection unit, and
an optical axis of the measurement light at the emission end surface is rotated by a predetermined angle to a side opposite to a side on which the acoustic wave detection unit is positioned around an intersection point of the emission end surface and the optical axis inside the light emission unit with respect to a normal direction of the detection surface of the acoustic wave detection unit.

9. The photoacoustic measurement apparatus according to claim 8, wherein the light emission unit reflects or refracts the measurement light to incline the optical axis at the emission end surface.

10. The photoacoustic measurement apparatus according to claim 8, wherein the acoustic wave detection unit is a transducer array having a plurality of acoustic wave detection elements, and,
the light emission unit includes a first light guide member which expands a propagation range of the measurement light in an array direction of the transducer array.

11. The photoacoustic measurement apparatus according to claim 10, wherein an optical axis in the first light guide member is parallel to the normal direction.

* * * * *